United States Patent [19]

Rhodes

[11] Patent Number: 5,022,756

[45] Date of Patent: Jun. 11, 1991

[54] METHOD AND APPARATUS FOR SPECTROCHEMICAL ANALYSIS HAVING MAXIMUM REPEATABILITY

[75] Inventor: Robert P. Rhodes, Lincoln University, Pa.

[73] Assignee: Hewlett-Packard Company, Palo Alto, Calif.

[21] Appl. No.: 431,504

[22] Filed: Nov. 3, 1989

[51] Int. Cl.⁵ ............................................. G01N 21/73
[52] U.S. Cl. ................................ 356/316; 219/121.49; 315/111.21
[58] Field of Search ............. 356/316; 315/50, 111.21, 315/111.41, 111.51, 111.71, 112, 117; 219/121.49

[56] References Cited

U.S. PATENT DOCUMENTS

| Re. 32,626 | 3/1988 | Yoshizawa et al. | 315/111.21 |
| 4,509,855 | 4/1985 | Gay | 356/316 |
| 4,654,504 | 3/1987 | Sullivan et al. | 219/121 |
| 4,659,899 | 4/1987 | Welkie et al. | 315/111.21 |
| 4,776,690 | 10/1988 | Quimby | 356/72 |

Primary Examiner—F. L. Evans
Attorney, Agent, or Firm—Richard F. Schuette

[57] ABSTRACT

A method and apparatus for controlling measurement repeatability in spectrochemical analysis which analysis utilizes a plasma source is shown to include a plasma generator for providing energy to the plasma source to sustain plasma, a sensor for sensing the operating temperature of the plasma generator and a temperature controller for controlling the operating temperature of the plasma generator in response to the temperature sensed by the sensor. The temperature controller controls the operating temperature of the plasma generator either within a temperature range, such as between 100° C. or at a set point temperature. In the case of a magnetron having heat conductive fins as the plasma generator, the sensor senses the temperature of at least one of said fins and the temperature controller includes a fan directed to move air across the fins and a speed controller for controlling the speed of the fan in response to the sensed temperature of the fins.

24 Claims, 2 Drawing Sheets

METHOD AND APPARATUS FOR SPECTROCHEMICAL ANALYSIS HAVING MAXIMUM REPEATABILITY

FIELD OF THE INVENTION

The present invention relates to the field of chromatography analysis and, more particularly, to spectrochemical analysis which uses a plasma source detect elements or molecules contained in a sample compound which has been chromatographically separated.

BACKGROUND OF THE INVENTION

In analytical chemistry liquid chromatography (LC), gas chromatography (GC) and supercritical fluid chromatography (SFC) techniques have become important tools in the identification of chemical sample components. The basic principle underlying all chromatographic techniques is the separation of a sample chemical mixture into individual components by transporting the mixture in a moving fluid through a porous retentive media. The moving fluid is referred to as the mobile phase and the retentive media has been referred to as the stationary phase. One of the differences between liquid and gas chromatography is that the mobile phase is either a liquid or a gas, respectively.

In a gas chromatograph, typically, a supply of inert carrier gas (mobile phase) is continually passed as a stream through a heated column containing porous sorptive media (stationary phase). GC columns have also been known to comprise a hollow capillary tube having an inner diameter in the range of few hundred microns. A sample of the subject mixture is injected into the mobile phase stream and passed through the column. As the subject mixture passes through the column, it separates into its various components. Separation is due primarily to differences in the volatility characteristics of each sample component with respect to the temperature in the column. A detector, positioned at the outlet end of the column, detects each of the separated components as they exit the column.

In supercritical fluid chromatography, a fluid heated above the critical point, is used as the mobile phase. Such fluid is passed under pressure through a media, typically a capillary column, which differentially retains sample components. As the pressure of the mobile phase is increased, for example, from about 40 ATM to approximately 400 ATM, the sample being analyzed separates into its various components dependent upon the relative differential solubility of each component with the mobile phase. Since the mobile phase is a gas, detectors used in GC can be utilized a the outlet end of the column to detect the separated components as they exit.

In certain circumstances it is desirable to detect the actual elements or molecules present in each component, as each component exits the column. In such cases spectrochemical analysis is the choice detection technique. Such analysis typically utilizes atomic emission spectrometry detectors or mass spectrometers. Similar to other GC and SFC detectors, atomic emission detectors (AED) and mass spectrometers are typically positioned at the outlet end of the column to detect elements in the chromatographic effluents.

In such devices, a discharge tube is oriented to surround the outlet end of the column. An energy chamber is formed around portion of the discharge tube. A plasma generator is positioned to provide energy to the energy chamber to sustain plasma, for example, a magnetron positioned to provide microwave energy. The microwave energy causes a plasma discharge to be formed in the discharge tube. Chromatographic effluents entering the plasma are energized and separated into excited atoms or molecules. Excited ions escaping from the plasma are available as a source for mass spectrometry detection. As the electrons of the excited atoms or molecules return to their stable state, light is emitted which is unique to an element or molecular bond. In atomic emission detection, the light is separated into characteristic wavelengths and detected. For atomic emission detection, the detection process can also be described as monitoring and plotting as a function of time the atomic emission line for a particular element. The power output of the energy source, i.e., the magnetron, determines the intensity of the atomic emission line versus the concentration of the element in question. U.S. Pat. Nos. 4,654,504—Sullivan et al. and 4,776,690—Quimby describe and apply such AED devices.

The problem with such prior spectrochemical analysis devices is the ability of the detector to repeat measurements over time, i.e. day to day detector precision. In other words, the measurements made by such prior devices can vary from day to day depending on ambient laboratory conditions. Consequently, a need exists for a spectrochemical device having stable precision.

SUMMARY OF THE INVENTION

The advantages of the invention are achieved in a method and apparatus for controlling measurement repeatability in spectrochemical analysis which analysis utilizes a plasma source. In a preferred embodiment of the invention, the method and apparatus are shown to include a plasma generator for providing energy to the plasma source to sustain plasma, a sensor for sensing the operating temperature of the plasma generator and a temperature controller for controlling the operating temperature of the plasma generator in response to the temperature sensed by the sensor. In particularly preferred embodiments of the invention, the temperature controller controls the operating temperature of the plasma generator either within a temperature range, such as between 100° C. and 130° C. or at a set point temperature.

In the case of a magnetron having heat conductive fins as the plasma generator, the sensor senses the temperature of at least on of the fins and the temperature controller controls a fan directed to move air across the fins. The temperature controller controls the speed of the fan in response to the sensed temperature of the fins.

BRIEF DESCRIPTION OF THE DRAWINGS

The present invention will be better understood, and its numerous objects and advantages will become apparent by reference to the following detailed description of the invention when taken in conjunction with the following drawings, in which.

DETAILED DESCRIPTION OF THE PREFERRED EMBODIMENT

Figure 1:
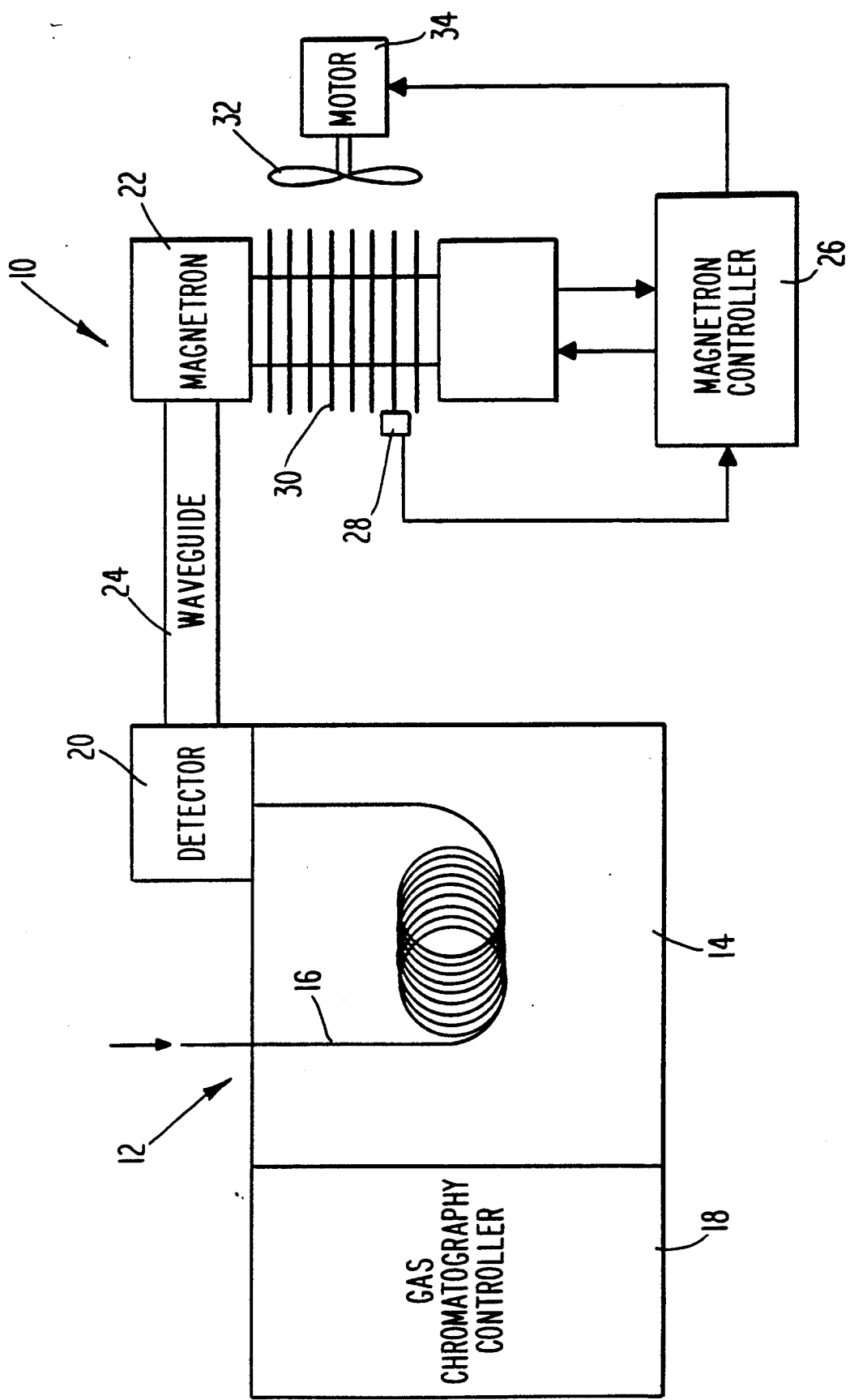
FIG. 1 is a block diagram of a gas chromatograph having an atomic emission spectrometer constructed in accordance with the present invention.

A new and novel atomic emission detector is shown in FIG. 1 and is generally designated 10. It will be noted at the outset that while for purposes of illustration the invention has been described in relation to an atomic emission detector, the invention has equal applicability to any spectrochemical analysis device which utilizes a plasma source in the detection scheme.

Detector 10 is utilized to determine elements in the effluent passing out of a gas chromatograph which is generally designated 12. Gas chromatograph 12 can be of any known design which includes an oven 14 and column 16. As will be appreciated, a sample compound to be analyzed is injected into the inlet end of column 16. Separated components or effluents are detected as they pass from the outlet end of column 16. Controller 18, which can also be of any known design, controls all of the dynamic operating parameters of gas chromatograph 12.

Atomic emission detector 10 is shown to include a detector section 20. Although detector section 20 can be of any known design, in order to practice atomic emission spectrometry it will be necessary for section 20 to include those components necessary to contain a plasma discharge and further to position the plasma discharge so that effluents passing out of Column 16 pass therethrough. Detector section 20 also detects and analyze light emitted from effluents passing through such plasma. In the preferred embodiment, such plasma is sustained by microwave energy provided by magnetron 22.

Microwaves generated by magnetron 22 are provided to detector section 20 via waveguide 24. Waveguide 24 can be of any know construction. It is within the scope of the present invention to provide microwave energy generated by magnetron 22 to detector section 20 by any suitable technique. As used in the present application, magnetron 22 can also be referred to as a plasma generator in that the microwaves generated by magnetron 22 serve to sustain the plasma discharge.

As indicated previously, the power output of the magnetron determines the intensity of a so-called emission line when a certain amount of an element under investigation is present, i.e., when that element is excited by the plasma discharge to the extent that it emits characteristic light. The output power of magnetron 22 is controlled by magnetron controller 26. It is known to control power output of magnetron 22 by controlling the voltage input. Accordingly, magnetron controller 26 includes any known circuitry for controlling the input voltage to magnetron 22.

As indicated previously, the repeatability of measuring the intensity of an atomic emission line versus element concentration can vary from day to day. This condition occurs despite precise control of magnetron input voltage. I have discovered that by controlling the operating temperature of the magnetron, which in the preferred embodiment involves maintaining the operating temperature of the magnetron within a prescribed range, repeatability can be maximized. To this end, a sensor 28 is positioned to sense the operating temperature of the plasma generator. Magnetrons ar typically provided with a heat sink containing one or more thermally conductive fins. Such fins normally act to remove heat resulting from the microwave generation process. In the preferred embodiment, sensor 28 is a platinum resistance thermometer which is affixed to one or more fins 30 of magnetron 22. The temperature of fins 30 is utilized in connection with the invention as the operating temperature of magnetron 22.

The operating temperature of magnetron 22 is controlled by removing more or less heat from magnetron 22. The removal of heat is accomplished in the preferred embodiment by moving more or less air across fins 30. Air is moved across fins 30 by operation of fan 32. Fan 32, in turn, is operated by variable speed motor 34. Although motor 34 can be of any known design, in the preferred embodiment, increase or decrease in voltage to motor 34 should result in an increase or decrease in the rotational speed of fan 32. The voltage to motor 34 in the preferred embodiment is controlled by appropriate circuitry in magnetron controller 26 in response to the signal from sensor 28. Such circuitry is described in greater detail in relation to FIG. 3. The speed of fan 32 is regulated in response to the sensed temperature of fins 30.

Figure 2:
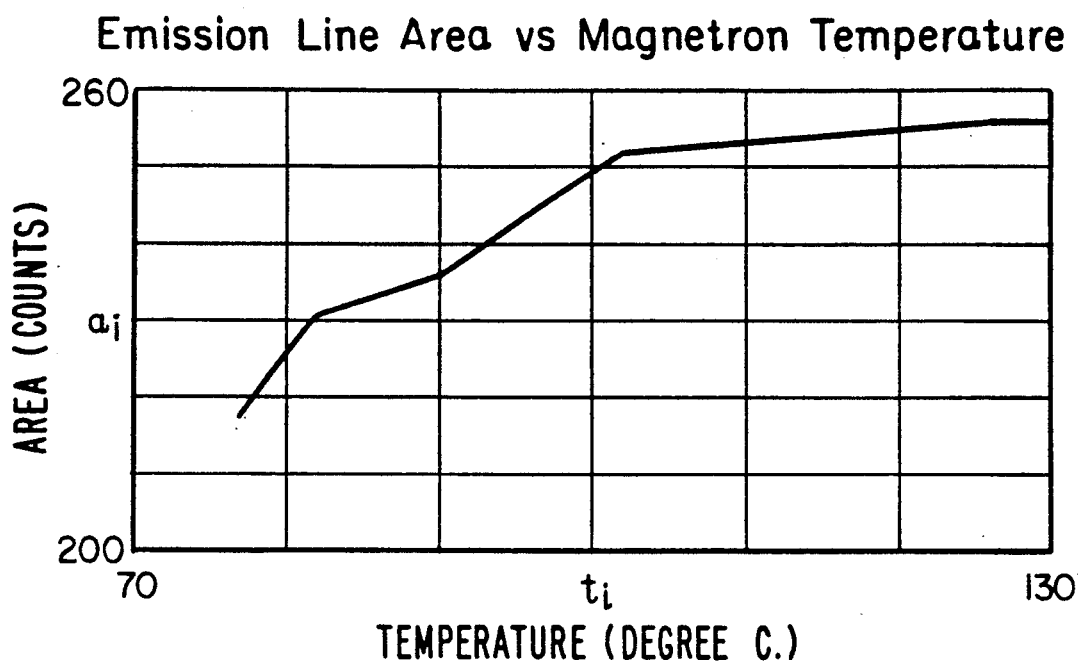
FIG. 2 is a graph of emission line area versus magnetron temperature for the magnetron shown in FIG. 1.

Consider now more particularly measurement of the intensity of an atomic emission line in relation to the operating temperature of the magnetron. In FIG. 2 a graph is depicted between emission line area and magnetron temperature. It should be noted that in the preferred embodiment magnetron 22 is a 2M211A magnetron by Panasonic. Also, as used in this application, emission line area refers to that area which exists beneath a graphed emission line in a atomic emission detector chromatograph for a subject element. As shown in FIG. 2, the emission line area for a given element will increase as the operating temperature of the plasma generator, i.e., magnetron 22, increases. It will also be noted however, that between 90° C. and 100° C. the emission line area increases at a much greater rate than the emission line area which exists between 100° C. and 130° C. In other words, if the magnetron operating temperature changes a few degrees within the range between 90° C. and 100° C., it will have a more significant impact on emission line area than the identical degree change in the range above 100° C. Accordingly, it is a further aspect of the present invention not only to control the magnetron operating temperature, but to maintain the magnetron temperature within a range between 100° C. and 130° C. In the preferred embodiment, magnetron temperature would be maintained at 130° C. By maintaining magnetron temperature in this fashion, emission line area is maximized from analysis to analysis and maintained relatively stable. In other words, the repeatability of measuring the intensity of the atomic emission line versus element concentration is controlled. It will be understood that controlling magnetron temperature in this fashion, resolves the problems inherent in prior devices, discussed above.

Figure 3:
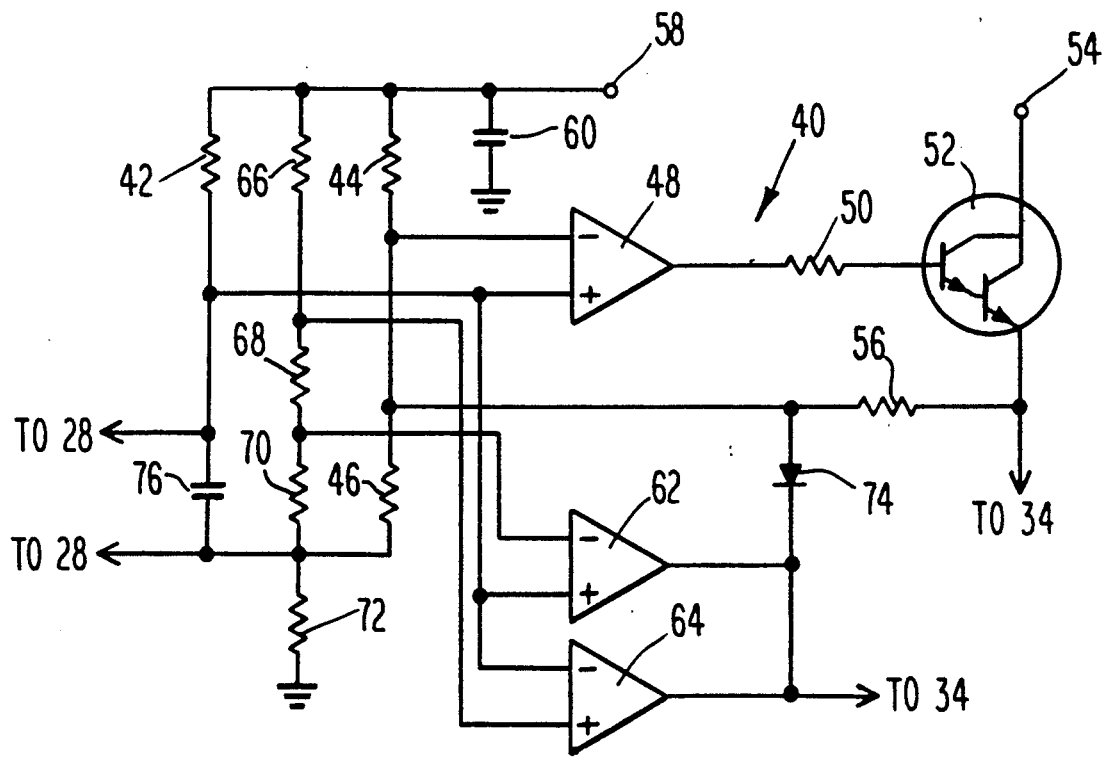
FIG. 3 is a schematic diagram of the temperature control circuit contained in the magnetron controller of FIG. 1.

Consider now particular circuit for controlling motor 34, which controls fan 32, which in turn regulates the movement of air across fins 30. It will be understood that the movement of more or less air across fins 30 will cause more or less heat to be removed from magnetron 22, thus controlling the operating temperature of magnetron 22. Such a circuit is shown in FIG. 3 and is generally designated 40.

Generally, sensor 28, a platinum resistance thermometer, is incorporated in the resistance bridge network comprising resistors 42, 44 and 46. The difference in voltage across the bridge network is sensed by differential amplifier 48. Resistor 50 is connected in series with the output of amplifier 48 and the base of Darlington transistor 52. It will be understood that as the voltage difference between the inputs of amplifier 48 change, the output of amplifier 48 will cause the Darlington transistor 52 to become more or less conductive. Thus, more or less of the supply voltage provided to terminal 54 will be supplied to motor 34. Resistor 56 is provided in the feedback loop between the emitter of Darlington transistor 52 and the negative input of amplifier 48.

The bridge network is energized by a second supply voltage provided to terminal 58. Capacitor 60 protects the bridge network from any spike voltages which may appear at terminal 58. Magnetron protection is provided through comparators 62 and 64. Comparators 62 and 64 serve to provide full fan power in the event of a failure, i.e., open or short circuit, of resistance thermometer 28. To this end, a voltage divider network including resistors 66, 68, 70 and 72 serves to establish voltage reference levels for comparators 62 and 64. Diode 74 establishes a voltage path between the outputs of comparators 62 and 64 with Darlington transistor 52. Capacitor 76, connected between the leads to resistance thermometer 28, prevents ambient high frequency signals from interfering with control circuit 40.

Consider now control circuit 40 during operation. As magnetron 22 provides microwave energy through waveguide 24 to detector 20, the operating temperature will increase and decrease depending upon the power output. The increase or decrease in operating temperature will be sensed by resistance thermometer 28. In turn, the resistance of sensor 28 will increase or decrease. As the resistance of sensor 28 increases, the voltage applied to the positive input of differential amplifier 48 will also increase. As the difference increases between the positive and negative input voltages to differential amplifier 48, the output of amplifier 48 will cause Darlington transistor 52 to become more conductive, which in turn, results in a greater voltage being applied to motor 34.

Conversely, as the resistance of sensor 28 decreases, less voltage is applied to the positive input of amplifier 48. As the difference between the positive and negative voltages decreases Darlington transistor 52 will become less conductive. Consequently, less voltage will be applied to motor 34. It should be noted that the values of resistors 44 and 46 will generally determine the temperature about which the operating temperature of magnetron 22 will be controlled.

In the event of a short circuit of sensor 28, the positive input of comparator 64 will exceed its negative input, resulting in a full power signal being supplied to motor 34. In the event of an open circuit of sensor 28, the voltage provided to the positive input to comparator 62 will exceed its negative input voltage, again resulting in a full power signal being applied to motor 34.

While the invention has been described and illustrated with reference to specific embodiments, those skilled in the art will recognize that modification and variations may be made without departing from the principles of the invention a described herein above and set forth in the following claims.

What is claimed is:

1. Apparatus for controlling measurement repeatability in spectrochemical analysis which analysis utilizes a plasma source, said apparatus comprising:
   a plasma generator for providing energy to said plasma source to sustain plasma;
   a sensor for sensing the operating temperature of said plasma generator; and
   temperature control means for controlling the operating temperature of said plasma generator in response to said sensor so that the repeatability is controlled.

2. The apparatus of claim 1, wherein said temperature control means controls the operating temperature of said plasma generator within a temperature range.

3. The apparatus of claim 1, wherein said temperature control means maintains the operating temperature of said plasma generator at a set point temperature.

4. The apparatus of claim 3, wherein said set point temperature is selected at a point where small changes in said operating temperature have relatively little effect on the spectrochemical analysis measurement.

5. The apparatus of claim 2, wherein said temperature range is between 100° C. and 130° C.

6. The apparatus of claim 1, wherein said plasma generator comprises a magnetron.

7. The apparatus of claim 6, wherein said magnetron has heat conductive fins and wherein said sensor senses the temperature of at least one of said fins.

8. The apparatus of claim 7, wherein said temperature control means comprises cooling means for cooling said fins.

9. The apparatus of claim 8, wherein said cooling means comprises a fan directed to move air across said fins and speed control means for controlling the speed of said fan in response to said sensor so that more or less air is moved across said fins to control said operating temperature.

10. The apparatus of claim 9, wherein said fan comprises an electric fan, wherein the speed of said fan is controlled by the voltage applied to said fan, wherein said sensor is a resistance thermometer and wherein said speed control means comprises a voltage control circuit which controls the voltage applied to said fan in response to the resistance of said resistance thermometer.

11. Apparatus for controlling measurement repeatability in spectrochemical analysis which analysis utilizes a plasma source having a magnetron as a plasma generator, said apparatus comprising:
    a sensor for sensing the operating temperature of said magnetron; and
    power output control means for controlling the power output of said magnetron in response to said sensor by controlling the operating temperature of said magnetron.

12. The apparatus of claim 11, wherein said power output control means comprises heat removal means for variably removing heat from said magnetron in response to said sensor.

13. The apparatus of claim 12, wherein said magnetron includes heat conductive fins and wherein said heat removal means comprises a fan whose speed is controlled by a speed control signal and a controller for generating said speed control signal in relation to the operating temperature sensed by said sensor.

14. A method for controlling measurement repeatability in spectrochemical analysis which analysis utilizes a plasma source, comprising the steps of:
    providing energy to said plasma source from a plasma generator to sustain plasma;
    sensing the operating temperature of said plasma generator; and controlling the operating temperature of said plasma generator in response to sensing the operating temperature so that the repeatability is controlled.

15. The method of claim 14, wherein the step of controlling the operating temperature controls the operating temperature of said plasma generator within a temperature range.

16. The apparatus of claim 14, wherein the step of controlling the operating temperature of said plasma generator comprises maintaining the operating temperature of said plasma generator at a set point temperature.

17. The apparatus of claim 16, wherein said set point temperature is selected at a point where small changes in said operating temperature have relatively little effect on the spectrochemical analysis measurement.

18. The method of claim 15, wherein said temperature range is between 100° C. and 130° C.

19. The method of claim 14, wherein said plasma generator comprises a magnetron having heat conductive fins and wherein the step of sensing the operating temperature of said plasma generator comprises the step of sensing the temperature of at least one of said fins.

20. The method of claim 19, wherein the step of controlling the operating temperature of said plasma generator comprises the step of cooling said fins.

21. The method of claim 20, wherein the step of cooling said fins comprises the steps of moving air across said fins by a fan and controlling the speed of said fan in response to sensing said operating temperature so that more or less air is moved across the fins to control the operating temperature.

22. The method of claim 21, wherein said fan comprises an electric fan, wherein said sensor is a resistance thermometer and wherein the step of controlling the speed of said fan comprises the step of regulating the voltage applied to said fan in response to the resistance of said resistance thermometer.

23. A method for controlling measurement repeatability in spectrochemical analysis which analysis utilizes a plasma source having a magnetron as a plasma generator, said method comprising the steps of:

sensing the operating temperature of said magnetron; and controlling the power output of said magnetron in response to said sensor by controlling the operating temperature of said magnetron.

24. The apparatus of claim 23, wherein said step of controlling the power output of said magnetron comprises variably removing heat from said magnetron in response to said sensor.

* * * * *